(12) United States Patent
Freehauf et al.

(10) Patent No.: US 9,084,719 B2
(45) Date of Patent: *Jul. 21, 2015

(54) COMPOSITIONS AND METHOD FOR TREATING INFECTION IN CATTLE AND SWINE

(75) Inventors: Keith A. Freehauf, Stockton, NJ (US); Allan Weingarten, Westfield, NJ (US); Robert D. Simmons, Martinsville, NJ (US); Kanwal Jit Varma, Warren, NJ (US)

(73) Assignee: Intervet Inc., Summit, NJ (US)

( * ) Notice: Subject to any disclaimer, the term of this patent is extended or adjusted under 35 U.S.C. 154(b) by 857 days.

This patent is subject to a terminal disclaimer.

(21) Appl. No.: 13/224,739

(22) Filed: Sep. 2, 2011

(65) Prior Publication Data

US 2012/0077764 A1  Mar. 29, 2012

Related U.S. Application Data

(63) Continuation of application No. 10/857,695, filed on May 28, 2004, now Pat. No. 8,034,845.

(60) Provisional application No. 60/474,294, filed on May 29, 2003.

(51) Int. Cl.
| | |
|---|---|
| *A61K 31/10* | (2006.01) |
| *A61K 31/165* | (2006.01) |
| *A61K 31/21* | (2006.01) |
| *A61K 31/4015* | (2006.01) |
| *A61K 9/00* | (2006.01) |
| *A61K 31/16* | (2006.01) |
| *A61K 31/195* | (2006.01) |
| *A61K 31/655* | (2006.01) |
| *A61K 31/66* | (2006.01) |
| *A61K 47/14* | (2006.01) |
| *A61K 47/32* | (2006.01) |

(52) U.S. Cl.
CPC ............. *A61K 9/0019* (2013.01); *A61K 31/10* (2013.01); *A61K 31/16* (2013.01); *A61K 31/165* (2013.01); *A61K 31/195* (2013.01); *A61K 31/21* (2013.01); *A61K 31/4015* (2013.01); *A61K 31/655* (2013.01); *A61K 31/66* (2013.01); *A61K 47/14* (2013.01); *A61K 47/32* (2013.01); *Y10S 514/947* (2013.01)

(58) Field of Classification Search
CPC ..... A61K 31/10; A61K 31/165; A61K 31/21; A61K 31/4015
USPC ......................................................... 514/618
See application file for complete search history.

(56) References Cited

U.S. PATENT DOCUMENTS

| | | | |
|---|---|---|---|
| 2,671,748 A | 9/1954 | Crooks | |
| 4,235,892 A | 11/1980 | Nagabhushan | |
| 4,311,857 A | 1/1982 | Nagabhushan | |
| 5,082,863 A | 1/1992 | Apelian et al. | |
| 5,105,009 A | 4/1992 | Jommi et al. | |
| 5,663,361 A | 9/1997 | Towson et al. | |
| 5,965,603 A | 10/1999 | Johnson et al. | |
| 6,054,434 A | 4/2000 | Kropp | |
| 6,136,838 A | 10/2000 | Chern et al. | |
| 6,174,540 B1 | 1/2001 | Williams et al. | |
| 6,733,767 B2 | 5/2004 | Chern et al. | |
| 6,790,867 B2 | 9/2004 | Kohan et al. | |
| 7,041,670 B2 | 5/2006 | Boojamra et al. | |
| 7,153,842 B2 | 12/2006 | Hecker et al. | |
| 7,361,689 B2 | 4/2008 | Shuster et al. | |
| 7,572,777 B2 | 8/2009 | Hecker et al. | |
| 7,713,950 B2 | 5/2010 | Shuster et al. | |
| 7,786,329 B2 | 8/2010 | Towson | |
| 8,034,845 B2 | 10/2011 | Freehauf et al. | |
| 2002/0102280 A1 | 8/2002 | Anderson | |
| 2003/0216447 A1 | 11/2003 | Kohan et al. | |
| 2004/0242546 A1 | 12/2004 | Freehauf et al. | |
| 2007/0055066 A1 | 3/2007 | Towson | |
| 2007/0055067 A1 | 3/2007 | Towson | |
| 2007/0155799 A1 | 7/2007 | Glinka et al. | |
| 2008/0145317 A1 | 6/2008 | Tongiani et al. | |
| 2008/0146640 A1 | 6/2008 | Glinka | |
| 2008/0153906 A1 | 6/2008 | Celly et al. | |
| 2008/0188556 A1 | 8/2008 | Glinka et al. | |
| 2008/0319200 A1 | 12/2008 | Towson | |
| 2009/0062397 A1 | 3/2009 | Tongiani | |
| 2009/0156683 A1 | 6/2009 | Simmons et al. | |
| 2009/0170954 A1 | 7/2009 | Towson et al. | |
| 2009/0275662 A1 | 11/2009 | Barbot | |
| 2010/0210851 A1 | 8/2010 | Towson | |

FOREIGN PATENT DOCUMENTS

| | | |
|---|---|---|
| CN | 1507858 A | 6/2004 |
| EP | 0 980 248 B1 | 10/2001 |
| WO | WO 02/41899 A1 | 5/2002 |
| WO | WO 03/097054 | 11/2003 |
| WO | WO 2004/089355 | 10/2004 |

OTHER PUBLICATIONS

Veterinary Pharmaceuticals and Biologicals, The Veterinarian's PDR, Veterinary Medicine Publishing Group, 1997/1998, p. 652.

Freedom of Information Summary, Original New Animal Drug Application, NADA 141-265 Sponsored by Schering-Plough Animal Health, Approved Mar. 21, 2008.

Madelenat, Racueil de Medicine Veterinare de lEcole d'Alfort, V. 173, No. 4-6, pp. 113-119, 1997.

*Primary Examiner* — Yong Chong

(57) ABSTRACT

Novel formulations containing a fluorinated chloramphenicol or thiamphenicol derivative antibiotic such as florfenicol, and methods for using such formulations in the treatment and prevention of infectious diseases of bovines and swine, including bovine respiratory disease.

9 Claims, 2 Drawing Sheets

COMPOSITIONS AND METHOD FOR TREATING INFECTION IN CATTLE AND SWINE

RELATED APPLICATIONS

This application is a Continuation under 37 CFR 1.53(b) of U.S. Non-Provisional application Ser. No. 10/857,695, filed on May 28, 2004, and which claims the benefit of U.S. Provisional Application No. 60/474,294, filed on May 29, 2003.

BACKGROUND OF THE INVENTION

The invention relates to compositions and methods for the treatment of bacterial infections in animals. More particularly, the invention relates to a composition containing an antibiotic for use in the treatment of bacterial infections in animals such as cattle, sheep and swine.

All references cited herein are hereby incorporated in their entirety by reference.

Widespread infection of cattle or other animals in a feedlot, the commingling of calves or other livestock from different sources causes the calves and other animals to be exposed to pathogens for which immunity has not developed. The stresses of shipping and change in diet reduces the calves' and other animals' immune defenses. Additionally, the poor weather of autumn, when calves or other livestock are usually moved from pastures to feedlots, further increases the risk of illness. Together, these circumstances result in a high incidence of respiratory disease in the cattle or other animals when they first arrive at the feedlot and soon thereafter. It has become common to administer antimicrobial drugs to calves and other feedlot animals at the time of arrival into a feedlot, in order to reduce the incidence and severity of respiratory illness in the feedlot cattle and other stock.

Without the use of antimicrobial agents, bovine respiratory disease (BRD), often referred to as the "bovine respiratory diseases complex" due to the multifactorial etiology has been one of the leading causes of economic loss to both the dairy and beef industries throughout the world. Excessive mortality, reduced weight gains, and the cost of treatment and prevention have placed a heavy burden on the industry.

The cost of death losses due to respiratory diseases vary around the world. Death losses in the U.S. are estimated to approach $1 billion annually. Losses in various European countries range from $75 to $120 million. Cattle with clinical or sub-clinical BRD do not gain weight or produce milk as well as healthy animals. Beef cattle with BRD gain less weight, have reduced feed efficiency and often produce a lower grade carcass at slaughter. Perino L. J. and Apley M., *Bovine Respiratory Disease, in* CURRENT VETERINARY THERAPY 4 (FOOD ANIMAL PRACTICE), 4$^{TH}$ ED., 446-455 (Howard J. L., Smith R. A., eds., 1999). A direct correlation between pulmonary lesions observed at slaughter and reduced weight gains has been established in cattle with sub-clinical infections. Whittem T. E. et al., *J. Am. Vet. Med. Assoc.*, 209:814-818 (1996).

In addition to the production losses associated with mortality and morbidity, significant costs are associated with the treatment of BRD due to the costs of various therapeutic agents and the labor required to administer these agents, along with the extra labor to isolate and observe these animals.

The pathogenesis of BRD is thought to be due to the interaction of environmental and physiological stresses coupled with infectious agents, such as *Mannheimia (Pasteurella) haemolytica, Pasteurella multocida* and *Haemophilus somnus* that are considered part of the normal flora of the bovine upper respiratory tract. When environmental and physiological stress factors reduce the natural resistance, and inhibit the pulmonary defense mechanisms, these above organisms proliferate and colonize the lower respiratory tract. In addition, various bovine viruses such as infectious bovine rhinotracheitis virus (IBRV), bovine viral diarrhea virus (BVDV), bovine respiratory syncytial virus (BRSV), and parainfluenza 3 virus (PI-3) are known to have immunosuppressive effects in the lung.

Similarly, swine respiratory disease (SRD) also has a multifactional etiology. Bacterial infections caused by *P. multocida, H. parasuis, Bordetella bronchiseptica, Actinobacillus pleuropneumoniae, Streptococcus suis, Salmonella cholerasuis* and *Mycoplasma* sp. may result in respiratory disease in swine, resulting in significant economic losses. Stresses such as crowding, mixing and moving of pigs and transient viral infections may contribute to the intensification of the disease.

Any of the pathogens listed as possibly implicated in BRD or SRD may stimulate an excessive inflammatory process in the lungs by producing various toxins that stimulate the release of various cytokines, which up-regulate the inflammatory process, resulting in death or morbidity. *M. haemolytica*, considered the most virulent of these various organisms, also produces a leukotoxin that inhibits phagocytosis by leukocytes, thus further enhancing its ability to colonize the lower respiratory tract. This process often results in a bacterial bronchopneumonia.

Damage to host tissues caused by invading pathogens occur as neutrophils, pulmonary alveolar macrophages and natural killer cells destroy infected cells. As cell membranes are damaged, arachidonic acid is released. Arachidonic acid is the substrate for the formation of various prostaglandins and other eicosanoids. The release of these biological active substances is critical to driving the inflammatory response that results in pulmonary lesions. Mosier D. A., *Vet. Clin. North Am. Food Animal Prac.*, 13:483-493 (1997).

In general, therapy for BRD should be directed at achieving the following goals:

1. Controlling the infection—In animals where the infectious process is halted early, the need for repeat treatment is significantly reduced (see Apley M. D. & Fejt V. R., *Vet. Clin. North Am. Food Anim. Prac.*, 14:291-313 (1998)). The selection of the appropriate antimicrobial compound should be based on the antimicrobial sensitivity of the organism involved, the levels of the antimicrobial agent in the respiratory tract, the ease of administration, the potential for injection site tissue damage, and a dosing regime that minimizes the pain and stress associated with treatment.

2. Minimize the pulmonary damage—As the level of inflammation and subsequent pulmonary damage increases, the probability of repeat therapy increases and the rate of weight gain decreases. Lekeux P., *Bovine Practitioner*, 29:71-75 (1995); Scott P. R., *J. Dairy Sci.*, 76(2):414-420 (1993).

3. Reduce pyrexia (fever)—Controlling the infection and reducing the inflammation will reduce the pyrexia, thus increasing the potential for recovery. The feeling of well-being that accompanies the reduction of pyrexia may also improve the intake of nutrients by suppressing inappetence associated with disease and pyrexia.

For years, antimicrobial therapy has been the mainstay of BRD therapy. There are many effective antimicrobial agents currently available for the treatment of BRD. NUFLOR®, an injectable formulation of the broad-spectrum antibiotic florfenicol, has emerged as one of the leading antibiotics on a global basis. NUFLOR® may be administered subcutaneously as well as intramuscularly. It is indicated for the treatment and control of BRD associated with *M. haemolytica*, *P. multocida* and *H. somnus* as well as for the prevention of respiratory disease in cattle at high risk of developing BRD associated with these bacteria. NUFLOR® is also indicated for the treatment of bovine interdigital phlegmon (footrot, acute interdigital necrobacillosis, infectious pododermatitis) associated with *Fusobacterium necrophorum* and *Bacteroides melaninogenicus*.

There is a need for conveniently administered, stable compositions that may control and prevent the infections associated with bovine respiratory disease and other infectious diseases.

SUMMARY OF THE INVENTION

Figure 1:
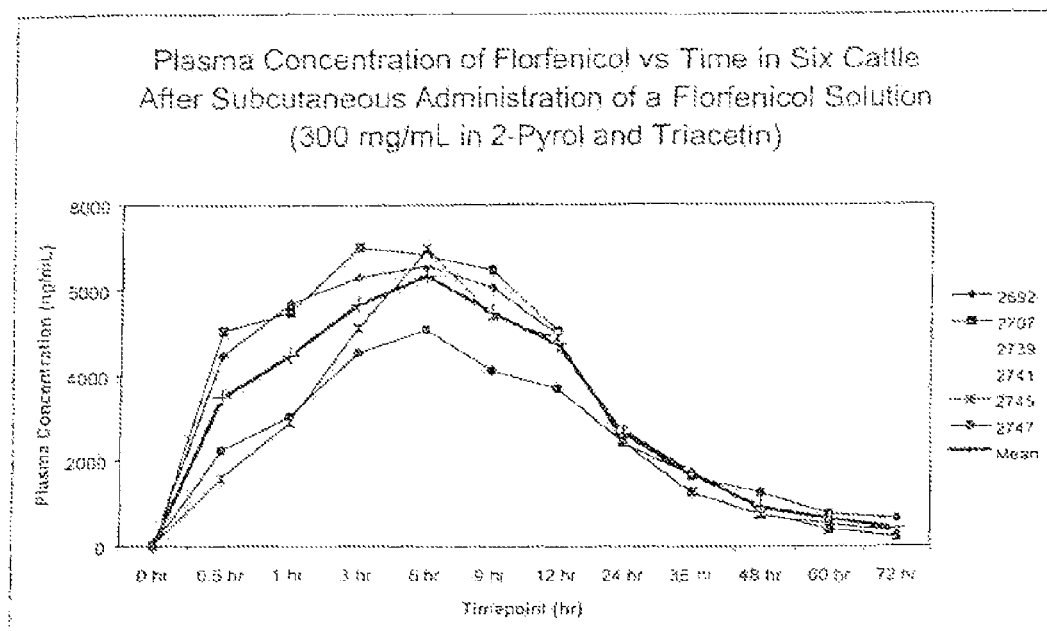
FIG. 1 is the plasma concentration of florfenicol vs. time in six cattle after subcutaneous administration of a florfenicol solution at a dose of 40 mg per kg of body weight. Mean peak concentration (Cmax) was 6366 ng/mL (range of 5076-6995 ng/mL). Mean time to peak concentration (Tmax) was 5.5 hrs (range of 3-6 hrs).

The present invention fulfills this need for a conveniently-administered, stable antibacterial product by providing improved compositions and methods for the treatment of respiratory disease, bacterial infection and other infections of cattle and other animals.

The present invention is also directed to a composition for the treatment of to microbial infection in an animal comprising
a) a Compound of Formula I:

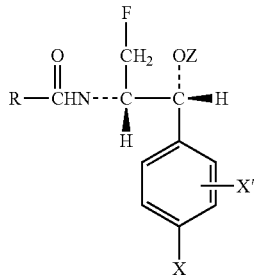

FORMULA I wherein R is a member selected from the group consisting of methyl or ethyl, or a halogenated derivative of either methyl or ethyl, dihalogenodeuteriomethyl, 1-halogeno-1-deuterioethyl, 1,2-dihalogeno-1-deuterioethyl, azidomethyl and methylsulfonylmethyl;

each of X and X' is a member independently selected from the group consisting of $NO_2$, $SO_2R_1$, $SOR_1$, $SR_1$, $SONH_2$, $SO_2NH_2$, $SONHR_1$, $SO_2NHR_1$, $COR_1$, $OR_1$, $R_1$, CN, halogen, hydrogen, phenyl, and phenyl mono-, di- or tri-substituted by halogen, $NO_2$, $R_1$, $PO_2R_1$, $CONHR_1$, $NHR_1$, $NR_1R_2$, $CONR_1R_2$, $OCOR_1$, or $OR_1$, wherein each of $R_1$ and $R_2$ is independently selected from the group consisting of methyl, ethyl, n-propyl, isopropyl butyl, t-butyl, isobutyl and phenyl;

and Z is hydrogen or an acyl group of a hydrocarboncarboxylic acid having up to 16 carbon atoms or an acyl group of an aminohydrocarboncarboxylic acid having up to 12 carbon atoms; and the pharmaceutically-acceptable salts of said acyl groups; and b) at least one carrier selected from the group consisting of triacetin, dimethylacetamide, 2-pyrollidone and combinations of the same.

Also disclosed is a method of treating bovine respiratory disease in an animal comprising the step of subcutaneously administering to an animal in need of such treatment a therapeutically-effective amount of the composition defined above wherein the plasma concentration of florfenicol over time after subcutaneous administration of a florfenicol solution at a dose of 40 mg/kg of body weight, is about 5000 to about 7000 ng/mL, and wherein the mean time to peak concentration is about 3 to about 6 hrs.

Also disclosed is a method of treating bovine respiratory disease in an animal comprising the step of subcutaneously administering to an animal in need of such treatment a therapeutically-effective amount of the composition defined above, wherein the plasma concentration of florfenicol over time after subcutaneous administration of a florfenicol solution at a dose of 40 mg/kg of body weight, is about 3400 to about 5000 ng/mL, and the mean time to peak concentration is about 1 to about 9 hrs.

DETAILED DESCRIPTION OF THE INVENTION

The invention provides novel compositions for the treatment of infectious diseases such as bovine respiratory disease in livestock. These compositions are formulations comprising certain antibacterial drugs, such as florfenicol, thiamphenicol, chloramphenicol in combination with unique and novel carriers and carrier systems.

The following terms will be defined as is known to one of skill in the art.

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as subsequently described. The bond to the parent moiety is through the carbonyl group. Preferred acyls contain a lower alkyl. Non-limiting examples of suitable acyl groups include formyl, acetyl, propanoyl, 2-methylpropanoyl, butanoyl and cyclohexanoyl.

"Alkyl" means an aliphatic hydrocarbon group, which may be straight or branched, comprising from 1 to about 20 carbon atoms in the chain. Preferred alkyl groups contain from 1 to about 12 carbon atoms in the chain. More preferred alkyl groups contain from 1 to about 6 carbon atoms in the chain. Branched means that one or more lower alkyl groups, such as methyl, ethyl or propyl, are attached to a linear alkyl chain. "Lower alkyl" means a group having from 1 to about 6 carbon atoms in the chain, which may be straight or branched. The term "substituted alkyl" means that the alkyl group may be substituted by one or more substituents which may be the same or different.

"Aryl" means an aromatic monocyclic or multicyclic ring system comprising about 6 to about 14 carbon atoms, preferably about 6 to about 10 carbon atoms. The aryl group may be optionally substituted with one or more "ring system substituents," which may be the same or different, and are as defined herein.

"Alkoxy" means an alkyl-O— group in which the alkyl group is as previously described. Non-limiting examples of suitable alkoxy groups include methoxy, ethoxy, isopropoxy, and n-butoxy. The bond to the parent moiety is through the ether oxygen.

"Azido" refers to an —N$_3$ group.

"Halo" and "halogeno" mean fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" and "halogenoalkyl" mean an alkyl group as defined above wherein one or more hydrogen atoms on the alkyl is replaced by a halo group defined above.

"Ring system substituent" means a substituent attached to an aromatic or non-aromatic ring system which, for example, replaces an available hydrogen on the ring system. Ring system substituents may be the same or different.

The term "optionally substituted" means optional substitution with the specified groups, radicals or moieties.

The term "composition" is intended to encompass a product comprising the specified ingredients in the specified amounts, as well as any product which results, directly or indirectly, from combination of the specified ingredients in the specified amounts.

An "effective amount" is the dose required to alleviate a particular symptom of an infection, infestation or disease or to protect an animal against infections, infestations or diseases and the term "bovine" refers to animals of the genus Bos, such as cattle. The term "bovid" refers to animals in the family Bovidae, which includes hoofed, hollow-horned ruminants such as cattle, sheep, goats, buffaloes, oxen, etc. As used herein, the term "swine" refers to animals of the family Suidae, which includes pigs, boars, warthogs, etc.

Fluorine-containing analogs of antibiotics chloramphenicol and thiamphenicol have been shown to have antibiotic activity, both against organisms sensitive to and resistant to chloramphenicol and thiamphenicol. See Schafer, T. W. et at, "Novel Fluorine-Containing Analogs of Chloramphenicol and Thiamphenicol: Antibacterial and Biological Properties," in CURRENT CHEMOTHERAPY AND INFECTIOUS DISEASE PROCEEDINGS OF THE 11$^{TH}$ ICC AND THE 19$^{TH}$ ICAAC AMERICAN SOCIETY OF MICROBIOLOGY 1980, 444-446. Examples of such compounds, and methods for their manufacture, are described and claimed in U.S. Pat. No. 4,235,892. The medical profession has become increasingly concerned about the transference of bacterial resistance to humans when antibiotics useful in treating humans are administered to livestock. Because the chloramphenicol group of antibiotics is infrequently used now to treat humans, its derivatives are particularly appropriate for veterinary use. Of particular interest are the 3-fluoro, 3-deoxy derivatives.

The compositions of the present invention comprise at least one antibiotic of Formula I:

FORMULA I

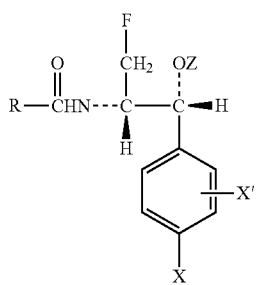

wherein R is a member selected from the group consisting of methyl, ethyl, or a halogenated derivative of methyl or ethyl, dihalogenodeuteriomethyl, 1-halogeno-1-deuterioethyl, 1,2-dihalogeno-1-deuterioethyl, azidomethyl and methylsulfonylmethyl;

each of X and X' is a member independently selected from the group consisting of NO$_2$, SO$_2$R$_1$, SOR$_1$, SR$_1$, SONH$_2$, SO$_2$NH$_2$, SONHR$_1$, SO$_2$NHR$_1$, COR$_1$, OR$_1$, R$_1$, CN, halogen, hydrogen, phenyl, and phenyl mono-, di- or tri-substituted by halogen, NO$_2$, R$_1$, OR$_1$, PO$_2$R$_1$, CONHR$_1$, NHR$_1$, NR$_1$R$_2$, CONR$_1$R$_2$ or OCOR$_1$, wherein each of R$_1$ and R$_2$ is a member independently selected from the group consisting of methyl, ethyl, n-propyl, isopropyl, butyl, t-butyl, isobutyl and phenyl;

and Z is hydrogen or an acyl group of a hydrocarboncarboxylic acid (preferably a hydrocarbondicarboxylic acid) having up to 16 carbon atoms or an acyl group of an aminohydrocarboncarboxylic acid having up to 12 carbon atoms; and pharmaceutically-acceptable salts of said acyl groups.

Included among the halogenated groups contemplated for the moiety R in Formula I are the mono-, di- and tri-fluoro, the mono-, di- and tri-chloro-, the mono- and di-bromo-, and the iodo-methyl groups, as well as the mono- and di-fluoro-, the mono- and di-chloro-, the mono- and di-bromo-, and the iodo-ethyl groups wherein the halogen substituents are preferably on the carbon alpha to the carbonyl function. Also included are mixed dihalogenoalkyl groups, in which both halogens are preferably bonded to the carbon alpha to the carbonyl groups, e.g., groups such as fluorochloro-, fluorobromo-, and chlorobromo-methyl and -ethyl, as well as trihalogen-methyl groups, such as dichlorofluoro- and difluorochloromethyl.

Also included among the compounds of Formula I are the ester derivatives, e.g., 1-hydrocarboncarboxylates of Formula I, wherein Z is an acyl group of a hydrocarboncarboxylic acid having up to 16 carbon atoms that may be saturated, unsaturated, straight-chain or branched-chain, aliphatic, cyclic, cyclic-aliphatic, aromatic, aryl-aliphatic, or alkyl-aromatic, and may be substituted by hydroxy, alkoxy containing from I to 5 carbon atoms, carboxyl, NO$_2$, NHR$_1$, NR$_1$R$_2$, SR$_1$, SOR$_1$, or halogen, wherein R$_1$ and R$_2$ are as defined above.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987), Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Other antibacterially-active ester derivatives of Formula I are those wherein Z is an acyl group of an amino acid containing up to 12 carbon atoms which may be saturated, unsaturated, straight chain, branched chain or cyclic, which may contain aromatic groups and that may be substituted by hydroxyl groups.

Preferred ester derivatives include those derived from dibasic hydrocarboncarboxylates, e.g., the 1-succinate and 1-palmitate esters, which provide water soluble, pharmaceutically-acceptable cationic salts, e.g., the sodium or potassium salts as well as salts with amine, e.g., trimethylamine. Also preferred are ester derivatives of amino acids that provide water soluble, pharmaceutically-acceptable acid addition salts with mineral or organic acids, e.g., the hydrochloric, or sulfuric acid, or succinic acid addition salts.

The term "pharmaceutically-acceptable salts" thus includes salts wherein the acidic hydrogen in the dibasic hydrocarboncarboxylate esters of this invention is replaced with a cation (e.g., sodium D-(threo)-1-p-nitrophenyl-2-dichloroacetamido-3-fluoro-1-propyl hemisuccinate) as well as salts wherein the acidic hydrogen forms an acid addition salt with an amine (e.g., D-(threo)-1-p-nitrophenyl-2-dichloroacetamido-3-fluoro-1-propyl hemisuccinate N-trimethylamine salt). Also included are the acid addition salts formed between mineral or organic acids and the amine in the amino acid esters of the compounds of Formula I (e.g., D-(threo)-1-p-nitrophenyl-2-dichloroacetamido-3-fluoro-1-propyl glycinate hydrochloride).

Among the pharmaceutically-acceptable cationic salts of the dibasic hydrocarboncarboxylate esters included in Formula I are salts of alkali and alkaline earth metals (e.g., sodium, potassium, calcium, aluminum) and salts with an amine, such as trialkylamines, procaine, dibenzylamine, N-benzyl-beta-phenethylamine, N,N'-dibenzylethylenediamine, N-(lower)alkylpiperidines (e.g., N-ethylpiperidine), and N-methyl glucamine.

Preferably R is a halogenated derivative of methyl or ethyl, Z is a hydrogen, X is phenyl, $COR_1$ or $SO_2R_1$, $R_1$ is methyl, and X' is hydrogen. Most preferably R is $CHCl_2$ or $CHF_2$.

A preferred antibiotic compound is florfenicol (D-(threo)-1-p-methylsulfonyl phenyl-2-dichloroacetamido-3-fluoro-1-propanol). Another preferred antibiotic compound is D-(threo)-1-p-methylsulfonyl phenyl-2-difluoroacetamido-3-fluoro-1-propanol. Processes for the manufacture of these preferred antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361. Another preferred antibiotic is thiamphenicol. The concentration of florfenicol or other antibiotic typically is from about 10% to about 50% w/v, with the preferred level between about 30% and about 40% w/v, even more preferred being at least about 30% w/v or 40% w/v.

A preferred vehicle for use in the present invention is triacetin. Triacetin is also known as 1,2,3 propanetriol triacetate, glyceryl triacetate and acetic, 1,2,3,-propanetriyl ester. Triacetin is available from, for example, Eastman Chemical. When triacetin is the vehicle, it may be present in a concentration of about 25% to about 90%, preferably at least about 30%. Alternatively, one could use triethylcitrate. It is believed that about 0% to about 5% of the florfenicol dissolves in triacetin. Preferably, triacetin is used in combination with 2-pyrrolidone as a co-vehicle or solvent. When 2-pyrrolidone is present in a co-vehicle or solvent, it may be present in a concentration of about 0% to about 70%, preferably about 30% w/v.

Another preferred carrier for use in the present invention is dimethylacetamide, also known as N,N'-dimethylacetamide, acetic acid dimethylamide and DMAC. Dimethylacetamide is available from BASF Corporation. When dimethylacetamide is a vehicle, it may be present in a concentration of about 0% to about 70%, preferably at least about 30% w/v.

The remaining portion of the formulations of the present invention may be a pharmaceutically-acceptable carrier comprising at least one solvent, carrier or vehicle. The pharmaceutically-acceptable carrier comprises from about 0% to about 80% of the formulation, preferably about 10% to about 30%, more preferably about 30%.

Accordingly, such vehicles (or a combination of such vehicles) is preferred for use in formulations of the present invention that contain florfenicol or similar antibiotics. Preferably such a solvent is present at about 0% to about 75% by weight of the formulation. More preferably such a solvent is present at about 10% to about 35% of the formulation.

Other pharmaceutically-acceptable solvents may be present in the formulations of the present invention. Suitable alternate solvents include, for example, glyceryl formal, dimethylformamide, N-Methyl-2-pyrrolidone, propylene glycol, polyethylene glycol (PEG), diethylisosorbide, water, ethanol, isopropanol, 1,2-propanediol, glycerin, benzyl alcohol, dimethylisosorbide, glycol ethers and the like.

The addition of one or more of such additional solvents or carriers may be desirable to reduce the viscosity of the formulation in order to provide a product with workable syringeability. Examples of solvents particularly useful for adjusting the viscosity of the formulations of the present invention include water, ethanol, isopropanol, propylene glycol, dimethylisosorbide, ethyl lactate and combinations thereof.

Other optional inert ingredients may be added to the present composition, as desired. Such ingredients include preservatives, chelating agents, antioxidants and stabilizers. Exemplary preservatives include methyl p-hydroxybenzoate (methylparaben) and propyl p-hydroxybenzoate (propylparaben). Exemplary chelating agents include edetate sodium. Exemplary antioxidants include butylated hydroxyanisole and sodium monothioglycerol. Preferred stabilizers for use in the present invention include, for example, citric acid in a concentration of about 5% or less and monothioglycerol in a concentration of about 0.1% to 2% w/v. Other suitable stabilizers include, for example, triethyl citrate, USP, NF, acetic acid, glacial acetic acid, fumaric acid, hydrochloric acid, diluted hydrochloric acid, malic acid, nitric acid phosphoric acid, diluted phosphoric acid, sulfuric acid and tartaric add. It will be appreciated that the formulations will preferable have an acidic pH. It will also be appreciated that the formulations of the present invention are self preserving.

It will be appreciated that other active ingredients may be combined with the formulations of the present invention. Such ingredients may include, for example, anti-inflammatory agents such as corticosteroids, NSAIDS, such as flunixin, COX—inhibitors and other analgesics, antiparasitic compounds such as, for example, an avermectin compound such as ivermectin, doramectin, milbemycin, selamectin, emamectin, eprinomectin, and moxidectin, and/or optionally a flukicide. It may also be preferred to employ a second antibiotic in the formulation. Preferred antibiotics may include tetracyclines. Particularly preferred is chlorotetracycline and oxytetracycline. Other preferred additional antibiotics include β-lactams, such as penicillins, cephalosporins, e.g., penicillin, amoxicillin, or a combination of amoxicillin with clavulanic acid or other beta lactamase inhibitors, ceftiofur, cefquinome, etc. Also preferred antibiotics include fluoroquinolones, such as, for example, enrofloxacin, danofloxacin, difloxacin, orbifloxacin and marbofloxacin, and macrolide antibiotics such as tilmicosin, tulathromycin, erythromycin, azithromycin and pharmaceutically-acceptable salts there of and the like. Alternatively, one could use insect growth regulators in combination with the formulations of the present invention.

In order to prepare the composition of the present invention, the vehicle(s) or a portion of the vehicle(s), are added to the compounding vessel, followed by the remaining excipients and the actives. The mixture is mixed until all solids are dissolved or in suspension. Additional solvent(s) to bring the composition to final volume may be added if needed. Additives, such as those listed above, may also be included in the vessel and mixed into the formulation (the order of addition is not critical).

The compositions according to the present invention will generally be administered to cattle at from about 1 mg to about 100 mg of the antibacterial agent(s) per kilogram of body weight. Preferably the compositions of the present invention will be administered to bovines at from about 20 mg to about 50 mg of the antibacterial agent(s) per kilogram of body weight. More preferably the dose will be about 40 mg/kg of the antibacterial agent administered once subcutaneously. Also preferable is the administration of two doses of 20 mg/kg administered at time 0 and 48 hours post initial administration. The compositions according to the present invention will generally be administered to swine at a dose of from 15 mg to about 100 mg of the antibacterial agent per kilogram of body weight. Preferably, the compositions of the present invention will be administered to swine at from about 20 mg to about 50 mg of the antibacterial agent per kilogram of body weight.

The compositions may be administered once daily or divided into multiple doses. Often only one dose will be sufficient to treat the infection. In some circumstances, one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The compositions according to the present invention are particularly useful for cattle and other bovids, swine, and other large mammals. In addition to the treatment of bovine respiratory disease, the compositions of this invention are also suitable for the treatment of infectious diseases such as swine respiratory disease, footrot, acute mastitis, pinkeye (infectious keratoconjunctivitis), acute pneumonia, metritis and enteritis. The dosage regimen for treatment of such diseases would be as described above.

Mastitis is a complex disease that occurs in lactating females, and is of particular economic importance in dairy cows and goats. Several pathogenic agents may be involved, including Staphylococcus aureus, E. coil, and streptococci. The acute form of mastitis has a sudden onset, the udder is enlarged, hot to the touch and tender; usually the affected animal will have a fever. If not treated promptly, the udder may be permanently damaged and milk production decreased or lost.

Pinkeye is an acute infectious disease of cattle, sheep and other animals that is characterized by inflammation of the tissues of the eye, accompanied by nasal discharge, lacrimation and copious ocular discharge. Affected animals may display extreme discomfort, resulting in a drop in milk production among dairy cattle; in extreme cases permanent blindness occurs. The disease, which is caused by *Moraxella bovis* in cattle, is widespread, especially among range and feedlot cattle, and is of great economic importance to the cattle industry.

Footrot (interdigital phlegmon) is an acute infection of the interdigital space that occurs throughout the world in both beef and dairy cattle. *Fusobacterium necrophorum* is the major cause of footrot, although other organisms, including *Bacteroides melaninogenicus*, may be involved. The major symptoms include pain, severe lameness, fever, anorexia, and reduced milk production.

Currently, footrot is treated by antibiotic therapy; recommended therapy may involve treatment for up to five days. The use of the formulations of the present invention for the treatment of footrot would be an improvement over presently known treatments because it would provide the proven efficacy of florfenicol, with fewer administrations. The compositions of the present invention are also useful for the prevention of these diseases in animals at high risk of developing those diseases. For example, the presently-claimed compositions may be administered to cattle at high risk of developing bovine respiratory disease at the same dosages recommended for treatment of bovine respiratory disease.

The formulations of the present invention have many significant advantages. The formulations containing triacetin and dimethylacetamide display an improved pharmacokinetic profile as well as sustained blood levels of florfenicol in the subject. In addition, a significant decrease in the variability of the subject-to-subject pharmacokinetic profiles and improved site reaction at the site of injection with less irritation and post injection inflammation were experienced. Further, the formulations display an improved chemical stability and are self-preserving. Also, particularly with dimethylacetamide, the formulations enable a lower injection volume with lower viscosity and hence improved syringeability. Preferably, the formulations of the present invention have a viscosity of less than about 125 cps.

The present invention will be further described by the following non-limiting examples.

Example 1

| Ingredient | Concentration | Percent by weight of formulation |
| --- | --- | --- |
| Florfenicol | 300 mg/ml | 30% w/v |
| 2-Pyrollidone | 300 mg/ml | 30% w/v |
| Triacetin | QS v/v | QS to 1 mL |

The ingredients may be mixed in a single or multiple steps. The florfenicol was mixed with 2-pyrrolidone and then triacetin was added to the mixture.

Example 2

| Ingredient | Concentration | Percent by weight of formulation |
| --- | --- | --- |
| Florfenicol | 400 mg/ml | 40% w/v |
| Dimethylacetamide | 300 mg/ml | 30% w/v |
| Triacetin | QS v/v | QS to 1 mL |

The ingredients may be mixed in a single or multiple steps. The florfenicol was mixed with dimethylacetamide and then triacetin was added to the mixture.

Example 3

Twenty-four head of cattle were used in the study as described below and were administered the formulations of the present invention. Serial blood samples were drawn at time 0 prior to dosing, then at 0.5, 1, 3, 6, 9, 12, 24, 36, 48, 60 and 72 hours post injection. The animals received one of the following treatment regimens.

TABLE 1

| Formulation Description | Dose[1] | number |
|---|---|---|
| 300 mg/mL in 2-pyrol and triacetin | 40 mg/kg SQ once in the side of the neck | 6 |
| 400 mg/mL in DMA and triacetin | 40 mg/kg SQ once in the side of the neck | 6 |

[1] no more than 10 ml per injection site

The injection site was assessed daily for the length, width and depth of the lesion and findings were recorded on the Lesion Evaluation Form.

The study was carried out in bovines of approximately 6 months of age or more that weigh about 125 kg or more. Selection was based on health status appearance, tractability and body weight. Animals exhibiting abnormal clinical signs prior to the start of the study were not included in the study. Animals that had received medication or have participated in another study in the previous 14 days were excluded from this study.

Baseline data was collected prior to initiating the study. Daily observations for clinical signs began on the first day of acclimation and continued until the study was terminated. All of the animals were weighed and physical examined, and health evaluation was conducted by a veterinarian on Day-7 (if acclimation is necessary) and on Day-1 if the cattle were already acclimated.

Plasma Levels of florfenicol were taken as follows: Approximately 10 mL of blood was collected from each calf by jugular venipuncture into a Vacutainer® tube containing sodium EDTA and processed for plasma.

Pharmacokinetic Analysis was carried out as follows: Plasma concentrations of florfenicol was reported in the appropriate units (i.e. µg/ml or ng/mL). Plasma florfenicol concentration versus time data was graphically presented for each individual animal, and as mean concentrations for the overall sample population.

Disclosed in FIG. 1 is the plasma concentration of florfenicol vs. time in six cattle after subcutaneous administration of a florfenicol solution at a dose of 40 mg to per kg of body weight. Mean peak concentration (Cmax) was 6366 ng/mL, preferably in a range of 5076-6995 ng/mL. Mean time to peak concentration (Tmax) was 5.5 hrs, preferably in a range of 3-6 hrs.

Figure 2:
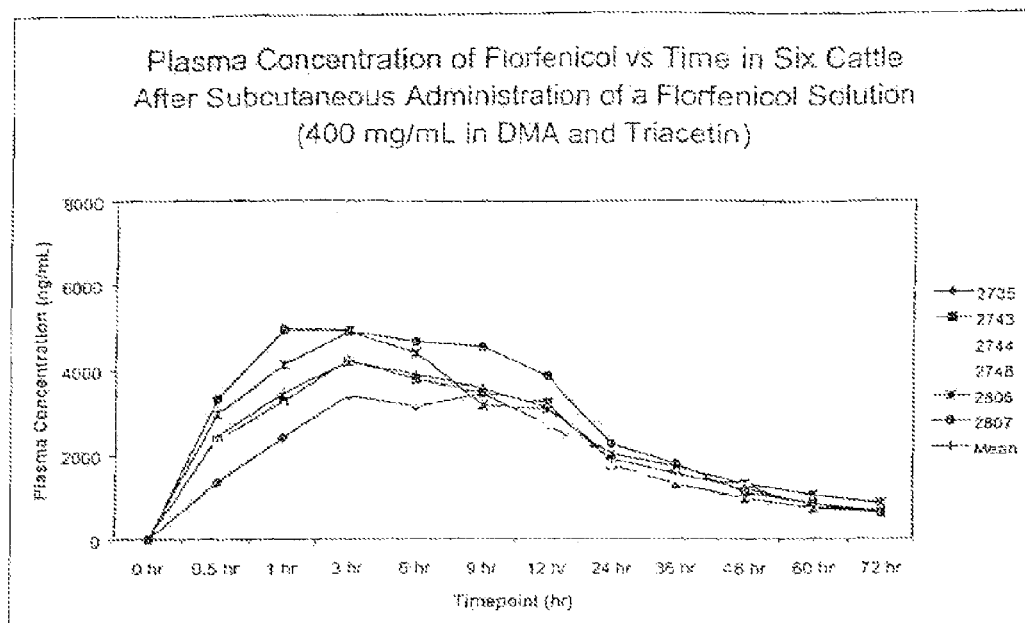
FIG. 2 is the plasma concentration of florfenicol vs. time in six cattle after subcutaneous administration of a florfenicol solution at a dose of 40 mg per kg of body weight. Mean peak concentration (Cmax) was 4248 ng/mL (range of 3457-4996 ng/mL). Mean time to peak concentration (Tmax) was 3.67 hrs (range of 1-9 hrs).

Disclosed in FIG. 2 is the plasma concentration of florfenicol vs. time in six cattle after subcutaneous administration of a florfenicol solution at a dose of 40 mg per kg of body weight. Mean peak concentration (Cmax) was 4248 ng/mL, preferably in range of 3457-4996 ng/mL. Mean time to peak concentration (Tmax) was 3.67 hrs, preferably in a range of 1-9 hrs.

This data displays that the formulations of the present invention have a number of substantial benefits. There is decreased tissue swelling at the site of injection. There is also a decrease in the volume of the injection that is administered. Also, there was low variation amongst subjects in the blood levels achieved.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A composition for the treatment of microbial infection in an animal consisting of florfenicol; and
   a) triacetin, and
   b) 2-pyrrolindone.

2. The composition of claim 1, wherein the florfenicol is present in an amount of about 10% to about 50% w/v.

3. The composition of claim 2, wherein the florfenicol is present in an amount of about 30% to about 40% w/v.

4. The composition of claim 1, wherein the triacetin is present in an amount of about 15% to about 60% w/v.

5. The composition of claim 4, wherein the triacetin is present in an amount of about 30% w/v.

6. The composition of claim 1, wherein the 2-pyrrolidone is present in an amount of about 30% w/v.

7. The composition of claim 1 further comprising a stabilizer.

8. The composition of claim 7, wherein the stabilizer is citric acid.

9. The composition of claim 1, wherein the composition has a viscosity of less than about 125 cps.

* * * * *